(12) United States Patent
Gorantla et al.

(10) Patent No.: US 9,895,377 B2
(45) Date of Patent: Feb. 20, 2018

(54) SOLID FORMS OF TYROSINE KINASE INHIBITORS, PROCESS FOR THE PREPARATION AND THEIR PHARMACEUTICAL COMPOSITION THEREOF

(71) Applicants: Seeta Ramanjaneyulu Gorantla, Hyderabad (IN); Ashwini Nangia, Andhra Pradesh (IN); Krishna Sumanth Peraka, Andhra Pradesh (IN); Udaya Bhaskara Rao Khandavilli, Hyderabad (IN)

(72) Inventors: Seeta Ramanjaneyulu Gorantla, Hyderabad (IN); Ashwini Nangia, Andhra Pradesh (IN); Krishna Sumanth Peraka, Andhra Pradesh (IN); Udaya Bhaskara Rao Khandavilli, Hyderabad (IN)

(73) Assignee: LAURUS LABS LIMITED, Andhra, Pradesh (IN)

( * ) Notice: Subject to any disclaimer, the term of this patent is extended or adjusted under 35 U.S.C. 154(b) by 217 days.

(21) Appl. No.: 13/948,578

(22) Filed: Jul. 23, 2013

(65) Prior Publication Data
US 2014/0031352 A1   Jan. 30, 2014

(30) Foreign Application Priority Data
Jul. 24, 2012   (IN) .......................... 3020/CHE/2012

(51) Int. Cl.
| | |
|---|---|
| *A61K 31/496* | (2006.01) |
| *A61K 31/506* | (2006.01) |
| *A61K 31/5377* | (2006.01) |
| *A61K 31/192* | (2006.01) |
| *A61K 47/12* | (2006.01) |
| *A61K 9/14* | (2006.01) |

(52) U.S. Cl.
CPC .......... *A61K 31/5377* (2013.01); *A61K 9/145* (2013.01); *A61K 31/192* (2013.01); *A61K 31/506* (2013.01); *A61K 47/12* (2013.01)

(58) Field of Classification Search
CPC .. C07D 239/94; C07D 237/32; C07D 241/52; A23K 1/1615; A23K 1/1628; A61K 31/496; A61K 31/506; A61K 31/5377; A61K 31/192
USPC .................. 544/119; 514/234.5, 252.18, 570
See application file for complete search history.

(56) References Cited

U.S. PATENT DOCUMENTS

| | | | |
|---|---|---|---|
| 6,894,051 B1 | 5/2005 | Zimmermann et al. | |
| 2005/0276836 A1* | 12/2005 | Wilson ................ | A61F 13/2051 424/422 |

FOREIGN PATENT DOCUMENTS

| | | | |
|---|---|---|---|
| CN | 102266300 A | * | 12/2011 |
| CN | 102266300 B | * | 1/2013 |
| EP | 0564409 A1 | | 10/1993 |
| EP | 0823900 B1 | | 2/1998 |
| WO | 2003072108 A1 | | 9/2003 |
| WO | 200575454 A2 | | 8/2005 |

OTHER PUBLICATIONS

Prasad, N., A. Karthiikeyan, S. Karthikeyan, B. V. Reddy "Inhibitory effect of caffeic acid on cancer cell proliferation by oxidative mechanism in human HT-1080 fibrosarcoma cell line" Mol. Cell. Biochem. (2011), 349, pp. 11-19.*

Prasad, N., A. Karthikeyan, S. Karthikeyan, B. V. Reddy "Inhibitory effect of caffeic acid on cancer cell proliferation by oxidative mechanism in human HT-1080 fibrosarcoma cell line" Mol. Cell. Biochem. (2011), 349, pp. 11-19.*

* cited by examiner

*Primary Examiner* — Matthew P Coughlin
*Assistant Examiner* — Sagar Patel
(74) *Attorney, Agent, or Firm* — Blank Rome LLP

(57) ABSTRACT

The present invention generally relates to solid forms of tyrosine kinase inhibitors, in particular combinations of tyrosine kinase inhibitors with anti-oxidative acids, processes for its preparation and a pharmaceutical compositions containing the same.

5 Claims, 14 Drawing Sheets

SOLID FORMS OF TYROSINE KINASE INHIBITORS, PROCESS FOR THE PREPARATION AND THEIR PHARMACEUTICAL COMPOSITION THEREOF

This application claims the priority of Indian Provisional Patent Application No. 3020/CHE/2012, filed Jul. 24, 2012, which is incorporated herein by reference.

FIELD OF THE INVENTION

The present invention generally relates to solid forms of tyrosine kinase inhibitors, in particular combinations of tyrosine kinase inhibitors with anti-oxidative acids, processes for its preparation and a pharmaceutical compositions containing the same.

BACKGROUND OF THE INVENTION

Tyrosine kinase inhibitor (TKI) is a pharmaceutical drug that inhibits tyrosine kinase, an enzyme which transports phosphates from ATP to a protein's tyrosine residue. Therefore, a Tyrosine Kinase inhibitor prevents the phosphate groups from being transferred. Research indicates that mutations which make Tyrosine Kinases constantly active can be a contributing factor in the development of cancerous cells. So, when an inhibitor is used, the cell communication and reproduction is reduced, and cancerous cell growth will be reduced to the point of stopping tumor growth.

Several TKIs have been found to have effective antitumor activity and have been approved and were commercially available in various dosage forms and strengths; for example imatinib, gefitinib, erlotinib, sorafenib, nilotinib, dasatinib, lapatinib, sunitinib, etc.

TKIs in pharmaceutical compositions can be prepared in a variety of different forms. Such drugs can be prepared so as to have a variety of different chemical forms including chemical derivatives or salts. Such drugs can also be prepared to have different physical forms. For example, the drugs may be amorphous or may have different crystalline polymorphs, perhaps existing in different solvates or hydrate states. By varying the form of a drug, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapour pressure, density, color, and compressibility.

EP Patent No. 0823900B1 discloses quinazoline derivatives such as Gefitinib of Formula I and pharmaceutically acceptable salts thereof viz. hydrochloride salt, dihydrochloride salt, difumarate salt, di-L-tartaric acid salt, dimethane sulfonic acid salt, disulfonic acid salt, di-4-toluene sulfonic acid salt.

Formula I

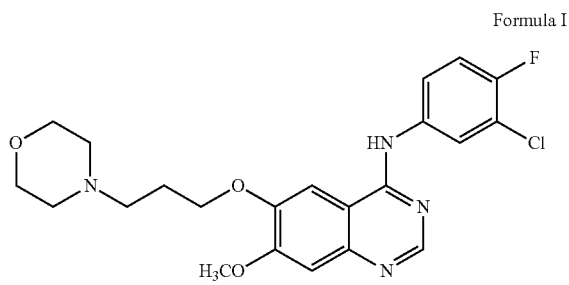 [SMILES: COc1cc2ncnc(Nc3ccc(F)c(Cl)c3)c2cc1OCCCN1CCOCC1]

PCT Publication WO 2003/072108, discloses crystalline forms of Gefitinib viz. Form-I anhydrous form, Form-2 MeOH solvate, Form-3 DMSO solvate and Form-5 trihydrate.

EP Patent No. 0564409 discloses Imatinib of Formula II and pharmaceutically acceptable salts thereof and process for the preparation of the same.

Formula II

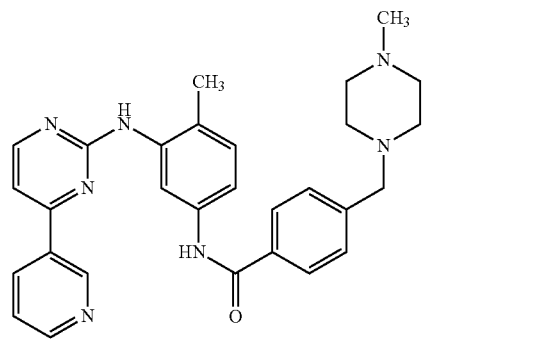

Imatinib is marketed in many countries as its methanesulfonate salt (imatinib mesylate) under the brand name GLIVEC® or GLEEVEC®. The marketed imatinib mesylate was disclosed in U.S. Pat. No. 6,894,051 ("the '051 patent") as its alpha-crystal form and a beta-crystal form. The '051 patent also discloses that the beta-crystal form has the advantage that its flow properties are substantially more favorable than those of the alpha-crystal form.

PCT Publication WO2005/075454 discloses various pharmaceutically acceptable salt forms of imatinib, which are exemplified by a tartrate salt (D,L), a hydrochloride salt, a citrate salt, a malate salt, a D-malate salt, a fumarate salt, a succinate salt, a benzoate salt, a benzenesulfonate salt, a pamoate salt, a formate salt, a malonate salt, a 1,5-naphthalenedisulfonate salt, a salicylate salt, a cyclohexanesulfamate salt, a lactate salt, a (S)-lactate salt, a mandelate salt, an (R)-(−)-mandelate salt, a glutarate salt, an adipate salt, a squarate salt, a vanillate salt, an oxaloacetate salt, an ascorbate salt, an (L)-ascorbate salt and a sulfate salt, and discloses a preparation method thereof and their water solubility. However, there is no disclosure about physical or pharmaceutical properties of the salts of imatinib.

Although it is known that the preparation of salt forms may improve the physical or pharmaceutical properties of a basic pharmaceutical active compound, it is not possible to predict which salt forms may possess advantages for a particular purpose prior to the actual preparation and characterization of the salt form.

The discovery of new salts and polymorphic forms of Tyrosine kinase inhibitors can provide new opportunities to improve the synthesis and the characteristics of the active pharmaceutical ingredient (API). Such discoveries can also enlarge the repertoire of materials that a formulation scientist has available for designing, for example, a pharmaceutical dosage form of a drug with a targeted release profile or other desired characteristic.

Accordingly, there remains a need in the art for novel solid forms of tyrosine kinase inhibitors having greater solubility and bioavailability and having desirable pharmacological, pharmacokinetic, pharmacodynamic effects.

SUMMARY OF THE INVENTION

It has now been surprisingly found that several chemically and morphologically stable novel solid forms of tyrosine kinase inhibitors and polymorphic forms thereof, in particular combinations of tyrosine kinase inhibitors with anti-oxidative acids could be prepared, in spite of the fact that a lot of salts of tyrosine kinase inhibitors and polymorphic forms thereof had already been known.

The objects of the present invention are the novel solid forms of tyrosine kinase inhibitor, in particular combinations of tyrosine kinase inhibitors with anti-oxidative acids, can be obtained which have improved properties as compared to presently-known form of such compounds. In an aspect, the improved property includes increased solubility, increased dissolution, increased bioavailability, increased dose response, decreased hygroscopicity, decreased form diversity, more desired morphology, and other property described herein.

Accordingly, in one embodiment, the present invention provides solid forms of a tyrosine kinase inhibitor and an anti-oxidative acid (herein after referred to as "solid forms of tyrosine kinase inhibitors").

In accordance with a second embodiment, the present invention provides solid forms of a tyrosine kinase inhibitor in combination with an anti-oxidative acid, where the tyrosine kinase inhibitor can be, but is not limited to, imatinib, gefitinib, erlotinib, sorafenib, nilotinib, dasatinib, lapatinib, sunitinib, or the like.

In accordance with a third embodiment, the present invention provides solid forms of a tyrosine kinase inhibitor in combination with an anti-oxidative acids, where the anti-oxidative acid can be, but is not limited to, benzoic acid derivatives such as p-hydroxy benzoic acid, vanillic acid, syringic acid, 3,4-dihydroxy benzoic acid and the like; or cinnamic acid derivatives such as p-coumaric acid, ferulic acid, sinapic acid, caffeic acid, and the like.

In accordance with a fourth embodiment, the present invention further provides the solid forms of tyrosine kinase inhibitors in the form of salts, polymorphs of salts, co-crystals, or polymorphs of co-crystals.

In accordance with a fifth embodiment, the present invention provides a process for preparing solid forms of tyrosine kinase inhibitors comprising a) providing a mixture or solution comprising tyrosine kinase inhibitors either in free base or an another salt form and an anti-oxidative acid; and b) isolating the solid forms of tyrosine kinase inhibitors; where the anti-oxidative acids are selected from the group consisting of benzoic acid derivatives such as p-hydroxy benzoic acid, vanillic acid, syringic acid, 3,4-dihydroxy benzoic acid and the like; cinnamic acid derivatives such as p-coumaric acid, ferulic acid, sinapic acid, caffeic acid and the like.

In accordance with a sixth embodiment, the present invention provides solid a forms of gefitinib in combination with an anti-oxidative acid.

In accordance with a seventh embodiment, the present invention provides a solid form of gefitinib in combination with an anti-oxidative acid, where the anti-oxidative acid can be, but is not limited to, benzoic acid derivatives such as p-hydroxy benzoic acid, vanillic acid, syringic acid, 3,4-dihydroxy benzoic acid and the like; or cinnamic acid derivatives such as p-coumaric acid, ferulic acid, sinapic acid, caffeic acid and the like.

In accordance with an eighth embodiment, the present invention provides solid forms of gefitinib and caffeic acid.

In accordance with a ninth embodiment, the present invention provides solid forms of gefitinib and p-coumaric acid.

In accordance with a tenth embodiment, the present invention provides solid forms of gefitinib and ferulic acid.

In accordance with an eleventh embodiment, the present invention provides solid forms of imatinib in combination with an anti-oxidative acid.

In accordance with a twelfth embodiment, the present invention provides solid forms of imatinib in combination with an anti-oxidative acid, where the anti-oxidative acids can be, but is not limited to, benzoic acid derivatives such as p-hydroxy benzoic acid, vanillic acid, syringic acid, 3,4-dihydroxy benzoic acid and the like; or cinnamic acid derivatives such as p-coumaric acid, ferulic acid, sinapic acid, caffeic acid and the like.

In accordance with a thirteenth embodiment, the present invention provides solid forms of imatinib and caffeic acid.

In accordance with a fourteenth embodiment, the present invention provides solid form of imatinib and caffeic acid at a 1:1 ratio.

In accordance with a fifteenth embodiment, the present invention provides solid form of imatinib and caffeic acid at a 1:2 ratio.

In accordance with a sixteenth embodiment, the present invention provides solid forms of imatinib and p-coumaric acid.

In accordance with a seventeenth embodiment, the present invention provides solid forms of imatinib and ferulic acid.

In accordance with an eighteenth embodiment, the present invention provides a solid form of a tyrosine kinase inhibitor which is characterized by one or more analytical techniques such as powder X-ray diffraction (PXRD) and differential scanning calorimetric (DSC) techniques, infrared spectra, nuclear magnetic resonance spectroscopy, among others.

In accordance with a nineteenth embodiment, the present invention provides a pharmaceutical composition comprising one or more of a therapeutically effective amount of solid forms of a tyrosine kinase inhibitor prepared by the processes of the present invention.

In accordance with a twentieth embodiment, the present invention provides a method of treating cancer by administering a pharmaceutical composition containing one or more of therapeutically effective amount of solid forms of tyrosine kinase inhibitors of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
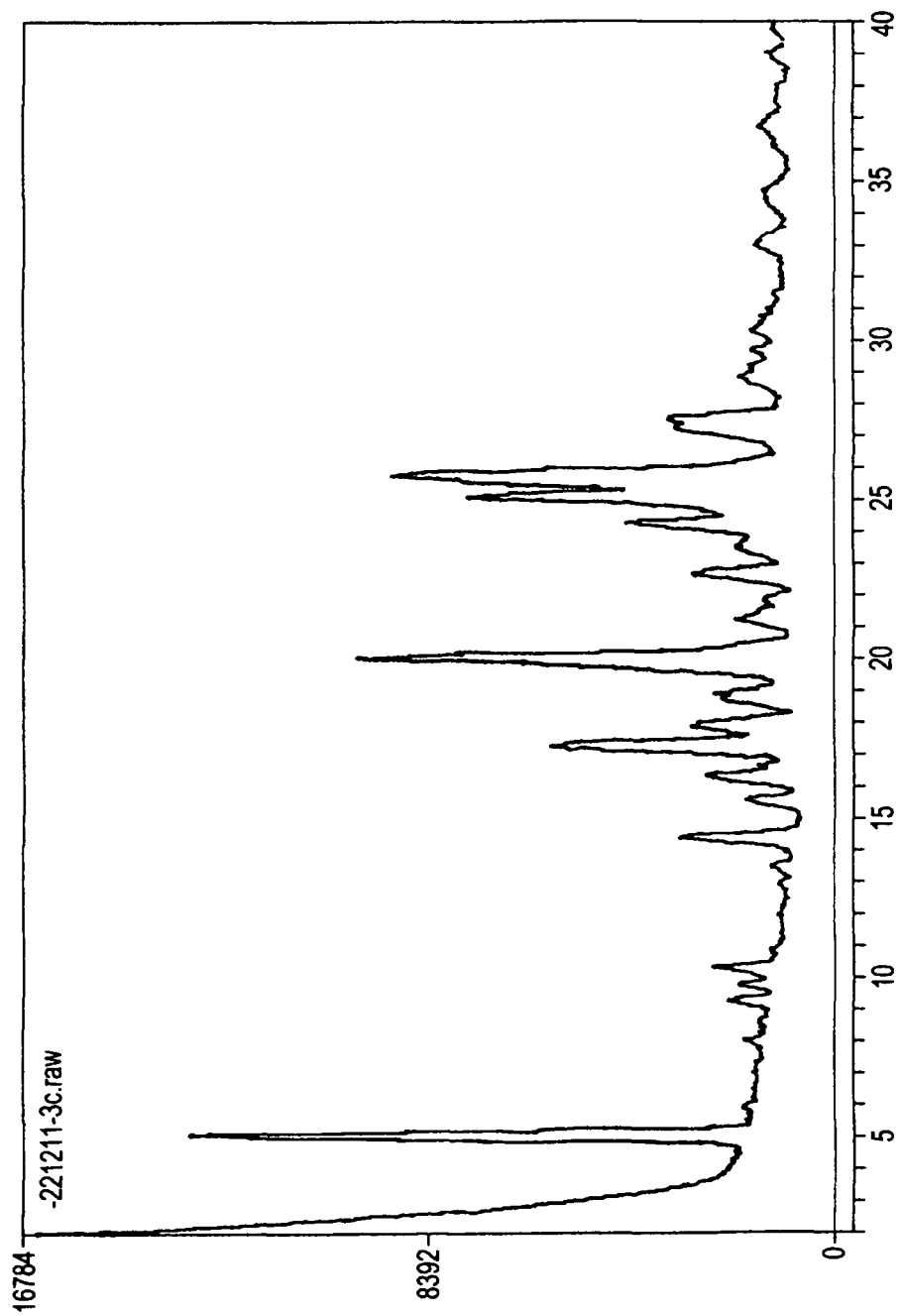
FIG. 1 is the characteristic powder X-ray diffraction (XRD) pattern of a solid form of gefitinib and caffeic acid (2:1).

The present invention addresses a need in the art by providing new solid forms of tyrosine kinase inhibitors; in particular combinations of tyrosine kinase inhibitors with anti-oxidative acids and processes for their preparation.

The present inventors have identified novel solid forms of tyrosine kinase inhibitors, particularly in combination with anti-oxidative acids. These solid forms may be in the form of salts, polymorphs of salts, co-crystals, or polymorphs of co-crystals.

It has surprisingly been found that when a tyrosine kinase inhibitor and a selected anti-oxidant acid component are allowed to form a solid form, the resulting solid form may give rise to improved properties of the tyrosine kinase inhibitors, as compared to its free form (including free base, hydrates, solvates etc.), particularly with respect to solubility, dissolution, bioavailability, stability, Cmax, Tmax, processability, longer lasting therapeutic plasma concentration, hygroscopicity, decrease in form diversity (including polymorphism and crystal habit), change in morphology or crystal habit, etc. For example, a solid form of tyrosine kinase inhibitor is particularly advantageous where the original tyrosine kinase inhibitor is insoluble or sparingly soluble in water. The solid form properties conferred upon the tyrosine kinase inhibitors are also useful because the bioavailability of the tyrosine kinase inhibitors can be improved and the plasma concentration and/or serum concentration of the tyrosine kinase inhibitors can be improved.

The anti-oxidant acids used in the present invention are not only intended for formation of pharmaceutically acceptable solid forms of tyrosine kinase inhibitors, but can advantageously be useful for therapeutical use, for example, the anti-oxidant acids can stabilize the body's metabolism by defending against damage caused by free radicals. The solid forms of tyrosine kinase inhibitors with anti-oxidant acids are more effective with respect to therapeutic activity of the tyrosine kinase inhibitors as compared to tyrosine kinase inhibitor solid forms without any anti-oxidant acid described in the prior art.

Accordingly, in one embodiment, the present invention provides solid forms of a tyrosine kinase inhibitor in combination with an anti-oxidative acids (herein after referred to as "solid forms of tyrosine kinase inhibitor").

The ratio of tyrosine kinase inhibitors to anti-oxidative acid compound may be stoichiometric or non-stoichiometric according to the present invention. For example, 1:1, 1.5:1, 1:1.5, 2:1 and 1:2 ratios of tyrosine kinase inhibitor to anti-oxidative acid are acceptable.

In another embodiment, the present invention provides solid forms of a tyrosine kinase inhibitor in combination with an anti-oxidative acid, where the tyrosine kinase inhibitor can be, but is not limited to, imatinib, gefitinib, erlotinib, sorafenib, nilotinib, dasatinib, lapatinib, sunitinib, or the like.

In another preferred embodiment, the present invention provides solid forms of a tyrosine kinase inhibitor in combination with an anti-oxidative acid, where the tyrosine kinase inhibitor is imatinib or gefitinib.

In another embodiment, the anti-oxidative acid is at least one of anti-oxidative acid compounds known in the art. For example, the anti-oxidative acid can be, but is not limited to benzoic acid derivatives such as p-hydroxy benzoic acid, vanillic acid, syringic acid, 3,4-dihydroxy benzoic acid, and the like; or cinnamic acid derivatives such as p-coumaric acid, ferulic acid, sinapic acid, caffeic acid, and the like.

It is known that the difference in delta pKa value of the tyrosine kinase inhibitor and the anti-oxidative acid indicate whether the anti-oxidative acid compound may form with tyrosine kinase inhibitor as salt form or co-crystals. As per the FDA draft guidelines, if the difference of delta pKa value is more than 3 then the compound may form as salt form whereas co-crystals may be formed if the delta pKa value is less than 3.

It has been found that the delta pKa difference between imatinib and anti-oxidative acids is found to be more than 3 and in the case of gefitinib and anti-oxidative acids is less than 3. The inventors of the present invention label imatinib may form salt with anti-oxidative acids whereas gefitinib may form co-crystals.

In another embodiment, the present invention provides a process for preparing solid forms of tyrosine kinase inhibitors, comprising a) providing a mixture or solution comprising a tyrosine kinase inhibitor either in free base or an another salt form and an anti-oxidative acid; and b) isolating the solid forms of tyrosine kinase inhibitor; wherein the anti-oxidative acid is selected from the group consisting of benzoic acid derivatives such as p-hydroxy benzoic acid, vanillic acid, syringic acid, 3,4-dihydroxy benzoic acid, and the like; and cinnamic acid derivatives such as p-coumaric acid, ferulic acid, sinapic acid, caffeic acid, and the like.

The step of forming a mixture or solution includes any form of tyrosine kinase inhibitor that may be combined in to a suitable solvent at a suitable temperature, then the anti-oxidant acid may be added to the resultant slurry or solution. Alternatively, the mixture may be formed by adding both the tyrosine kinase inhibitor and the anti-oxidative acid at the same time into a suitable solvent.

The suitable solvent can be, but is not limited to water, lower alcohols, esters, ethers, ketones, nitriles, aromatic hydrocarbons, halogenated hydrocarbons, amides, and the like, and mixtures thereof. The lower alcohols include, but is not limited to, methanol, ethanol, isopropanol, n-propanol, butanol, isobutanol, and the like; the esters include, but are not limited to, methyl acetate, ethyl acetate, isopropyl acetate, and the like; the ethers include, but are not limited to, diisopropyl ether, tetrahydrofuran, dioxane, methyl tertiary butyl ether, and the like; the ketones include, but are not limited to, acetone, methyl ethyl ketone, methyl isobutyl ketone, and the like; the nitriles include, but are not limited to, acetonitrile, propionitrile, and the like; the aromatic hydrocarbons include, but are not limited to, toluene, xylene, chlorobenzene, and the like; the halogenated hydrocarbons include, but are not limited to, methylene chloride, ethylene chloride, chloroform, carbon tetrachloride, and the like; the amides include, but are not limited to, dimethyl formamide, dimethyl acetamide, dimethyl sulfoxide, and the like.

In another embodiment, the present invention provides solid forms of gefitinib in combination with an anti-oxidative acid, where the anti-oxidative acid is selected from the group consisting of benzoic acid derivatives such as p-hydroxy benzoic acid, vanillic acid, syringic acid, 3,4-dihydroxy benzoic acid, and the like; and cinnamic acid derivatives such as p-coumaric acid, ferulic acid, sinapic acid, caffeic acid, and the like.

In a preferred embodiment, the present invention provides solid forms of gefitinib in combination with an anti-oxidative acid, wherein the anti-oxidative acid is selected from caffeic acid, p-coumaric acid, and ferulic acid.

In another embodiment, the present invention provides a process for preparation of solid forms of gefitinib combination with anti-oxidative acid, comprising: a) providing a mixture or solution comprising gefitinib either in free base or an another salt form and an anti-oxidative acid in a suitable solvent; and b) isolating the solid form of gefitinib, wherein the anti-oxidative acid is selected from caffeic acid, p-coumaric acid, and ferulic acid.

The suitable solvent can be, but is not limited to, water, lower alcohols, esters, ethers, ketones, nitriles, aromatic hydrocarbons, halogenated hydrocarbons, amides, and the like, and mixtures thereof, as described just above.

Step a) may be optionally carried out at a suitable temperature to effectively form a solid form of gefitinib. Typically the reaction temperature may be from about ambient temperature to about reflux temperature.

The resultant solid form of gefitinib can be isolated by crystallization, solvent precipitation, concentrated by subjecting the solution to heating, spray drying, freeze drying, evaporation on rotary evaporator under vacuum, agitated thin film evaporator (ATFE), or the like. The solid form of gefitinib can be recovered by any conventional technique known in the art, for example, filtration.

The solid forms of gefitinib recovered using the process of the present invention described above may include one or more of solid forms of gefitinib and caffeic acid, solid forms of gefitinib and p-coumaric acid, or solid forms of gefitinib and ferulic acid.

In another embodiment, the present invention provides a solid form of gefitinib and caffeic acid.

In another embodiment, the present invention further provides a solid form of gefitinib and caffeic acid, characterized by an X-Ray diffraction (XRD) pattern substantially in accordance with FIG. 1.

Figure 2:
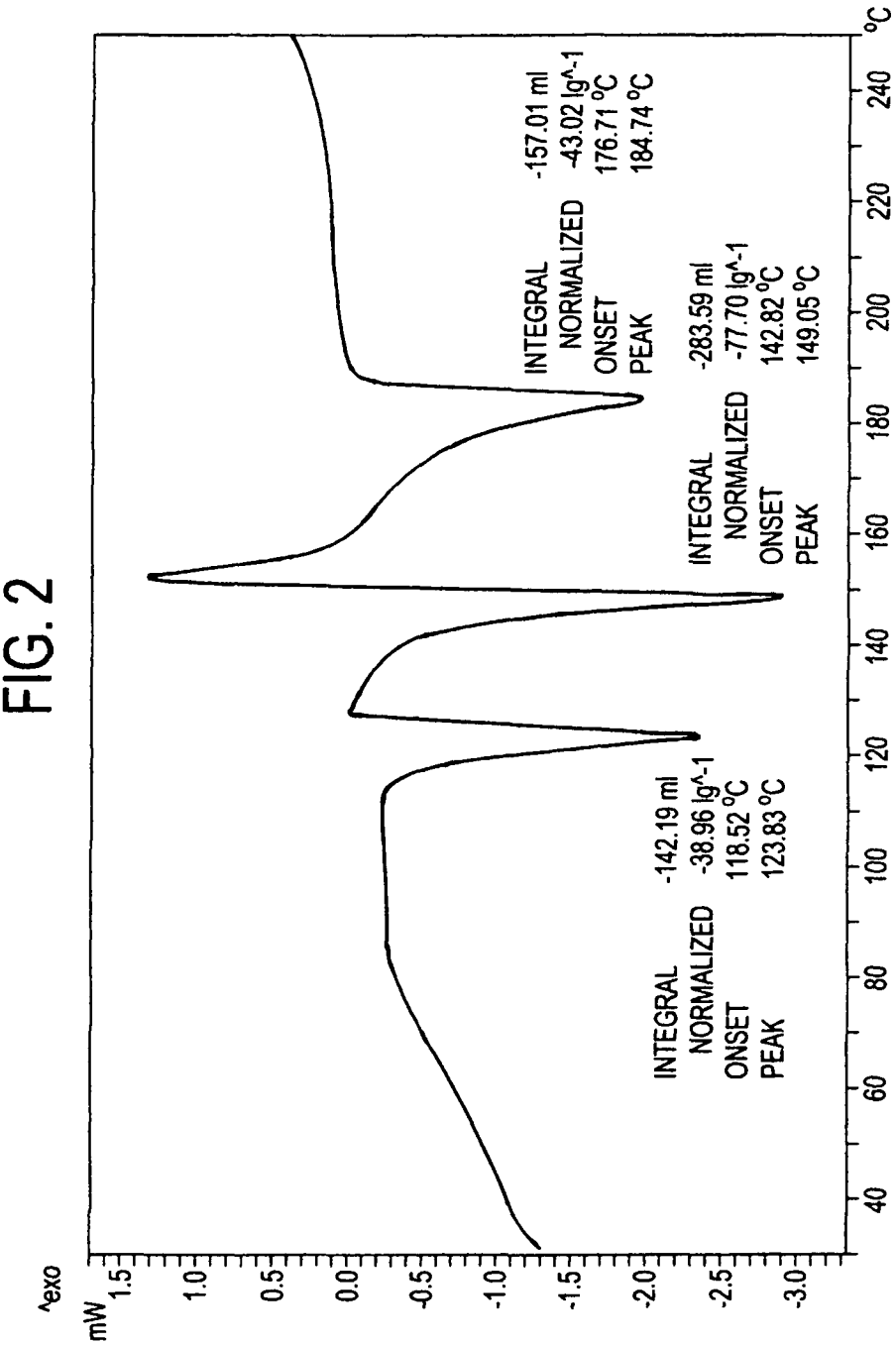
FIG. 2 is the characteristic differential scanning calorimetric (DSC) thermogram of a solid form of gefitinib and caffeic acid (2:1).

In another embodiment, the present invention further provides a solid form of gefitinib and caffeic acid, characterized by a differential scanning calorimetric (DSC) thermogram substantially in accordance with FIG. 2.

In another embodiment, the present invention provides a solid form of gefitinib and p-coumaric acid.

Figure 3:
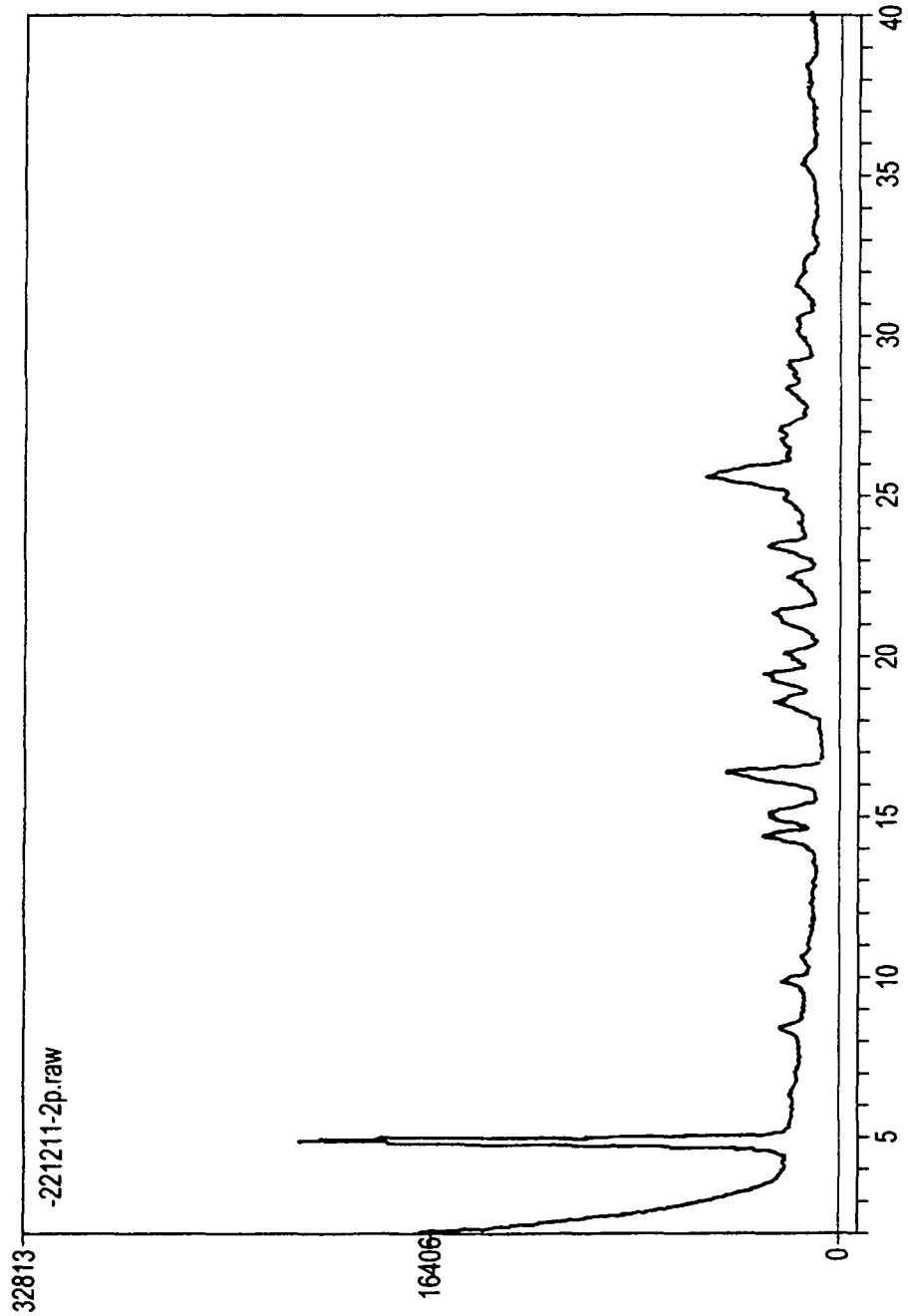
FIG. 3 is the characteristic powder X-ray diffraction (XRD) pattern of a solid form of gefitinib and p-coumaric acid (2:1).

In another embodiment, the present invention further provides a solid form of gefitinib and p-coumaric acid, characterized by an X-Ray diffraction (XRD) pattern substantially in accordance with FIG. 3.

Figure 4:
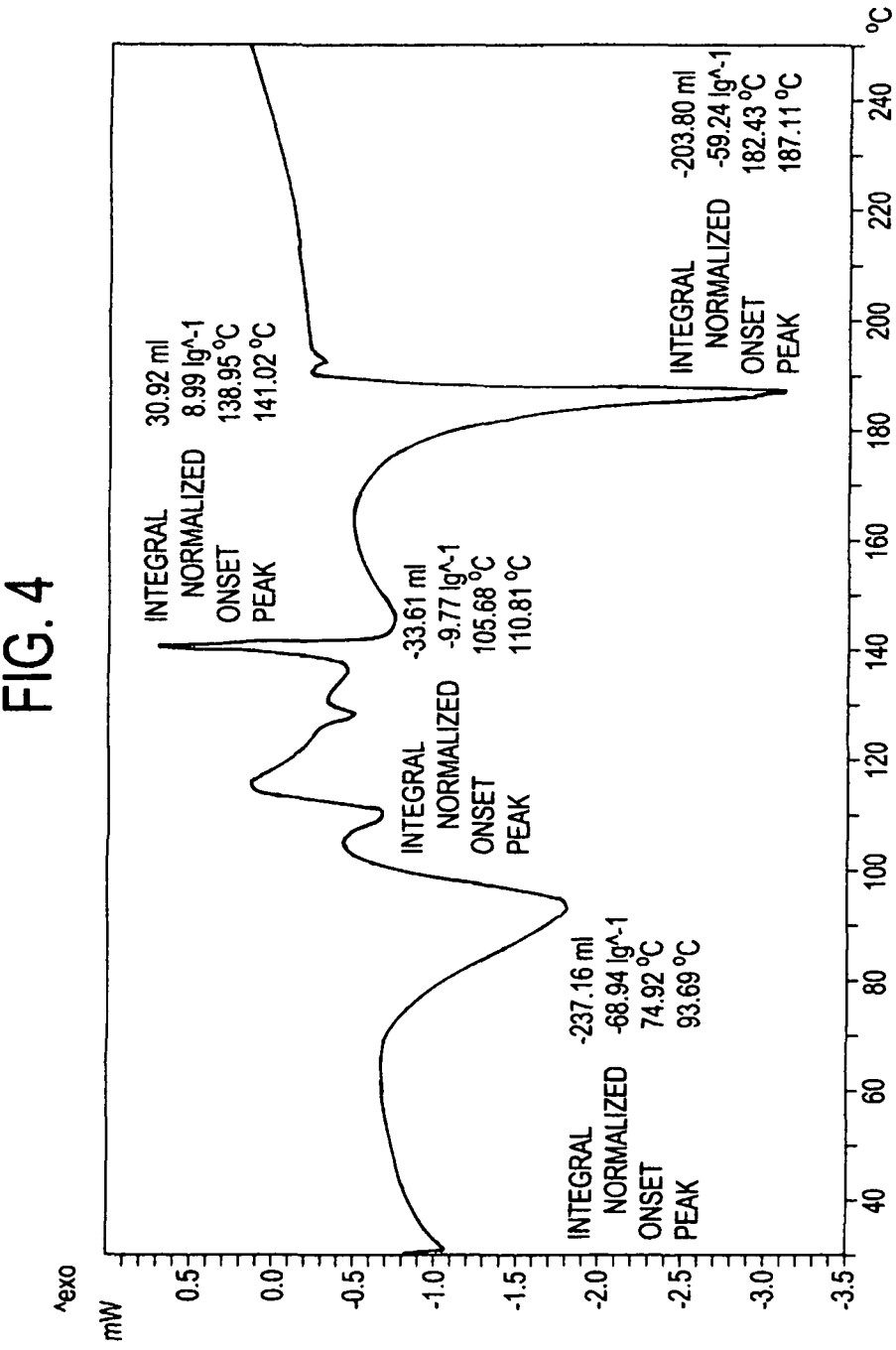
FIG. 4 is the characteristic differential scanning calorimetric (DSC) thermogram of a solid form of gefitinib and p-coumaric acid (2:1).

In another embodiment, the present invention further provides a solid form of gefitinib and p-coumaric acid, characterized by a differential scanning calorimetric (DSC) thermogram substantially in accordance with FIG. 4.

In another embodiment, the present invention provides a solid form of gefitinib and ferulic acid.

Figure 5:
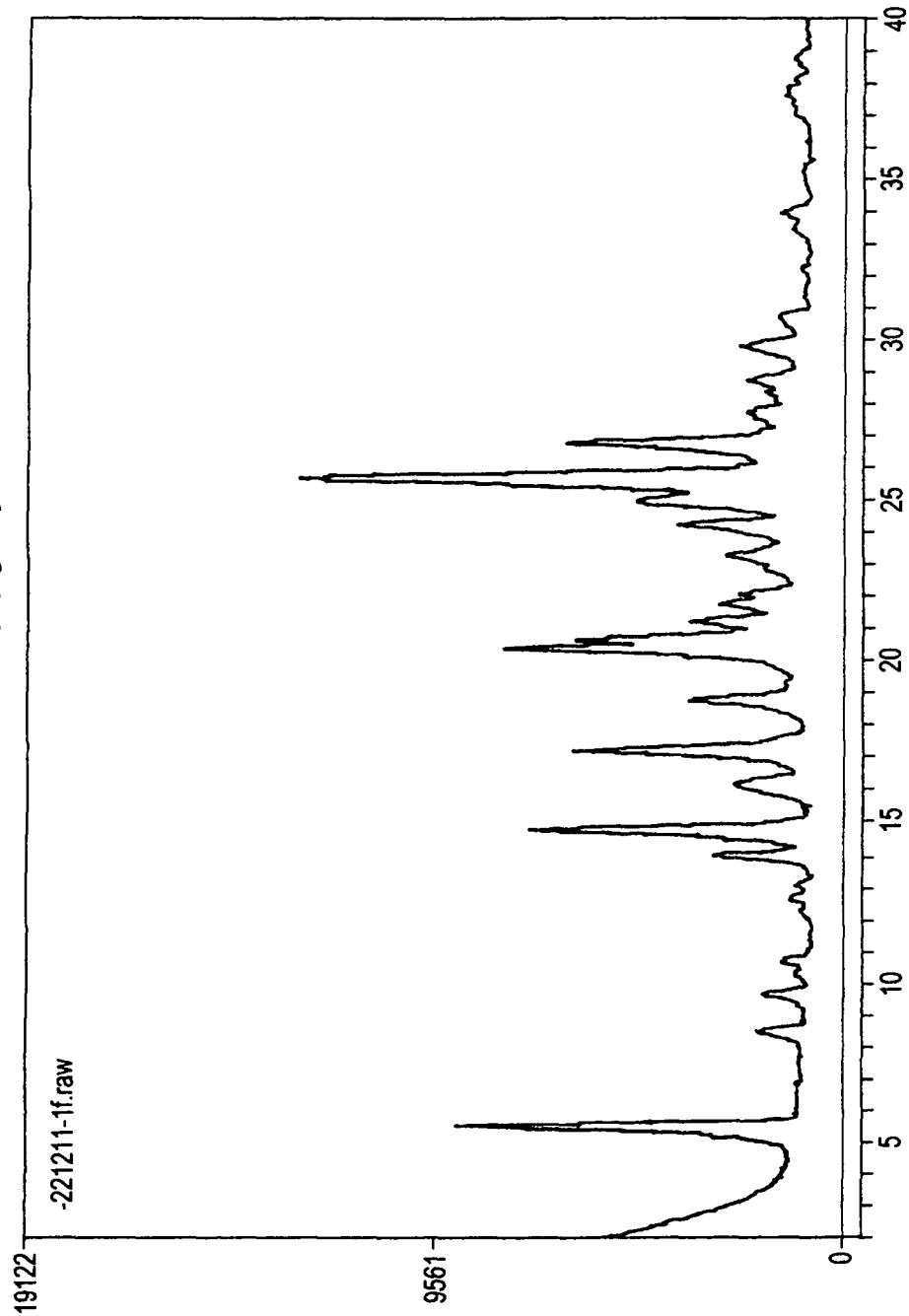
FIG. 5 is the characteristic powder X-ray diffraction (XRD) pattern of a solid form of gefitinib and ferulic acid (2:1).

In another embodiment, the present invention further provides a solid form of gefitinib and ferulic acid, characterized by an X-Ray diffraction (XRD) pattern substantially in accordance with FIG. 5.

Figure 6:
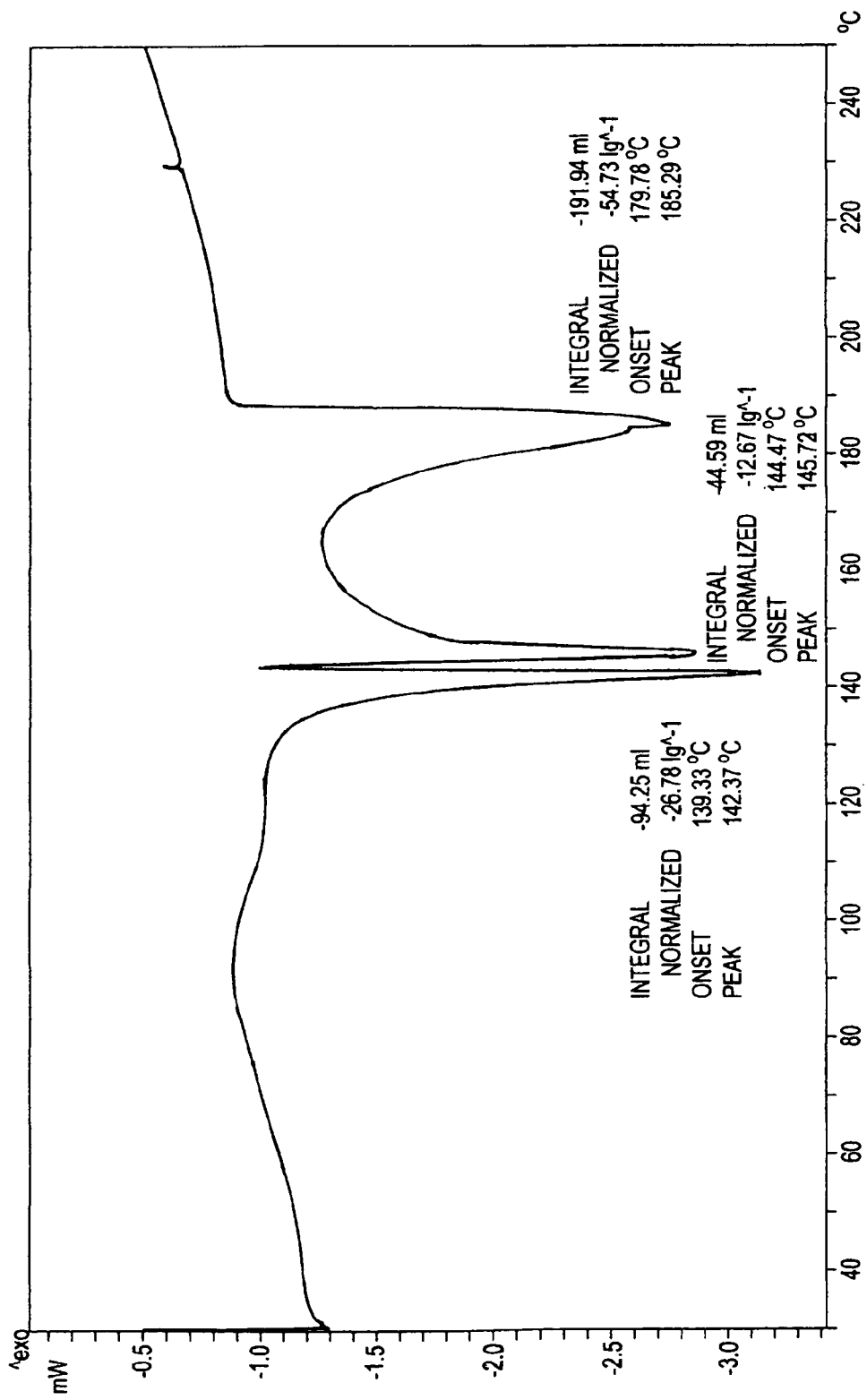
FIG. 6 is the characteristic differential scanning calorimetric (DSC) thermogram of a solid form of gefitinib and ferulic acid (2:1).

In another embodiment, the present invention further provides a solid form of gefitinib and ferulic acid, characterized by a differential scanning calorimetric (DSC) thermogram substantially in accordance with FIG. 6.

In another embodiment, the present invention provides solid forms of imatinib combination with an anti-oxidative acid, wherein the anti-oxidative acid is selected from the group consisting of benzoic acid derivatives such as p-hydroxy benzoic acid, vanillic acid, syringic acid, 3,4-dihydroxy benzoic acid, and the like; and cinnamic acid derivatives such as p-coumaric acid, ferulic acid, sinapic acid, caffeic acid, and the like.

In a preferred embodiment, the present invention provides solid forms of imatinib combination with anti-oxidative acid, wherein the anti-oxidative acid is selected from caffeic acid, p-coumaric acid, and ferulic acid.

In another embodiment, the present invention provides a process for preparation of solid forms of imatinib combination with anti-oxidative acid, comprising a) providing a mixture or solution comprising imatinib either in free base or an another salt form and an anti-oxidative acid in a suitable solvent; and b) isolating the solid form of imatinib; wherein the anti-oxidative acid is selected from caffeic acid, p-coumaric acid, and ferulic acid.

The suitable solvent includes, but are not limited to water, lower alcohols, esters, ethers, ketones, nitriles, aromatic hydrocarbons, halogenated hydrocarbons, amides, and the like, and mixtures thereof, as described above.

Step a) may be optionally carried out at a suitable temperature to effectively form solid forms of imatinib. Typically the reaction temperature may be from about ambient temperature to about reflux temperature.

The resultant solid form of imatinib can be isolated by crystallization, solvent precipitation, concentrated by subjecting the solution to heating, spray drying, freeze drying, evaporation on rotary evaporator under vacuum, agitated thin film evaporator (ATFE), and the like. The solid form of imatinib can be recovered by any conventional technique known in the art, for example, filtration.

The solid forms of imatinib recovered using the process of the present invention described above may include one or more of solid forms of imatinib and caffeic acid (1:1), solid forms of imatinib and caffeic acid (1:2), solid forms of imatinib and p-coumaric acid, and solid forms of imatinib and ferulic acid.

In another embodiment, the present invention provides a solid form of imatinib and caffeic acid (1:1).

Figure 7:
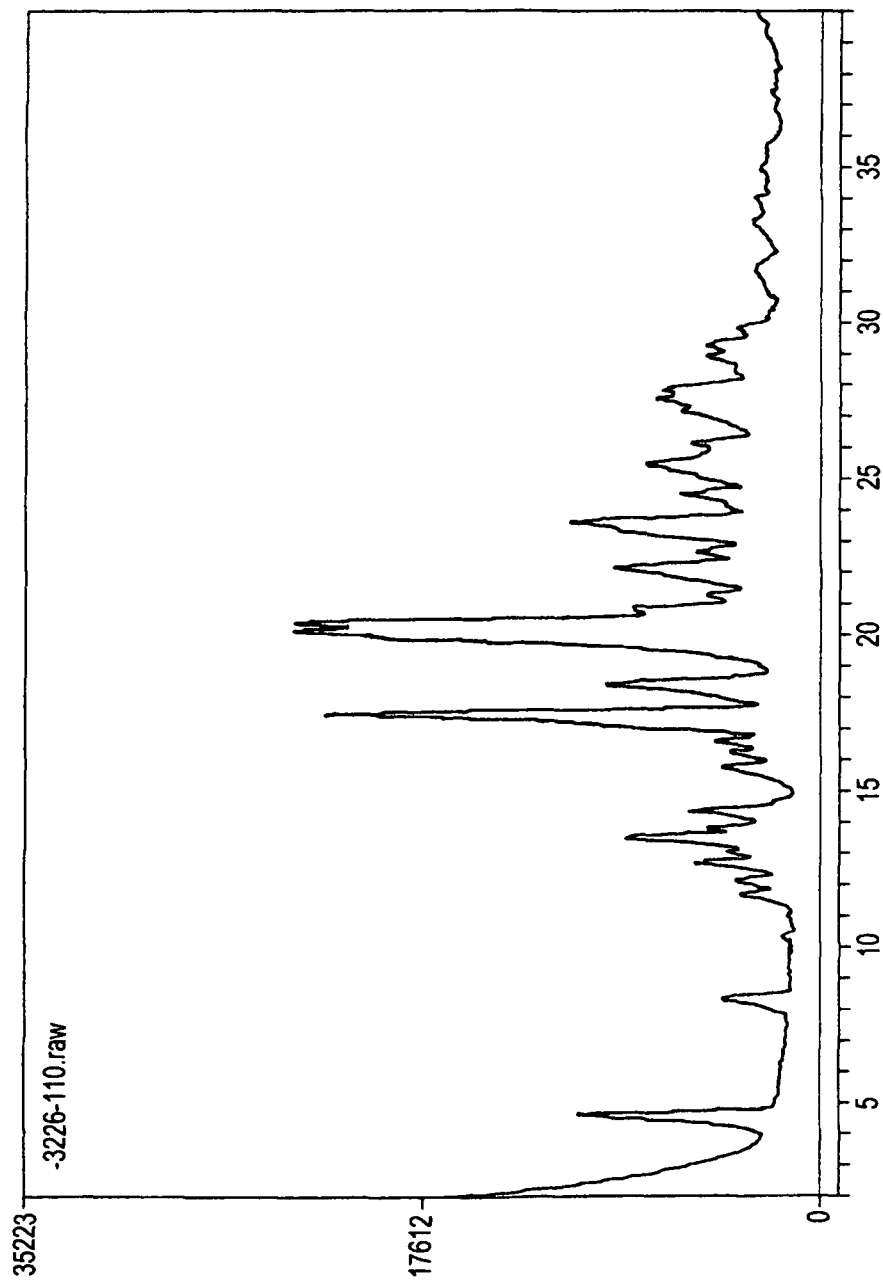
FIG. 7 is the characteristic powder X-ray diffraction (XRD) pattern of a solid form of imatinib and caffeic acid (1:1).

In another embodiment, the present invention further provides a solid form of imatinib and caffeic acid (1:1), characterized by an X-Ray diffraction (XRD) pattern substantially in accordance with FIG. 7.

Figure 8:
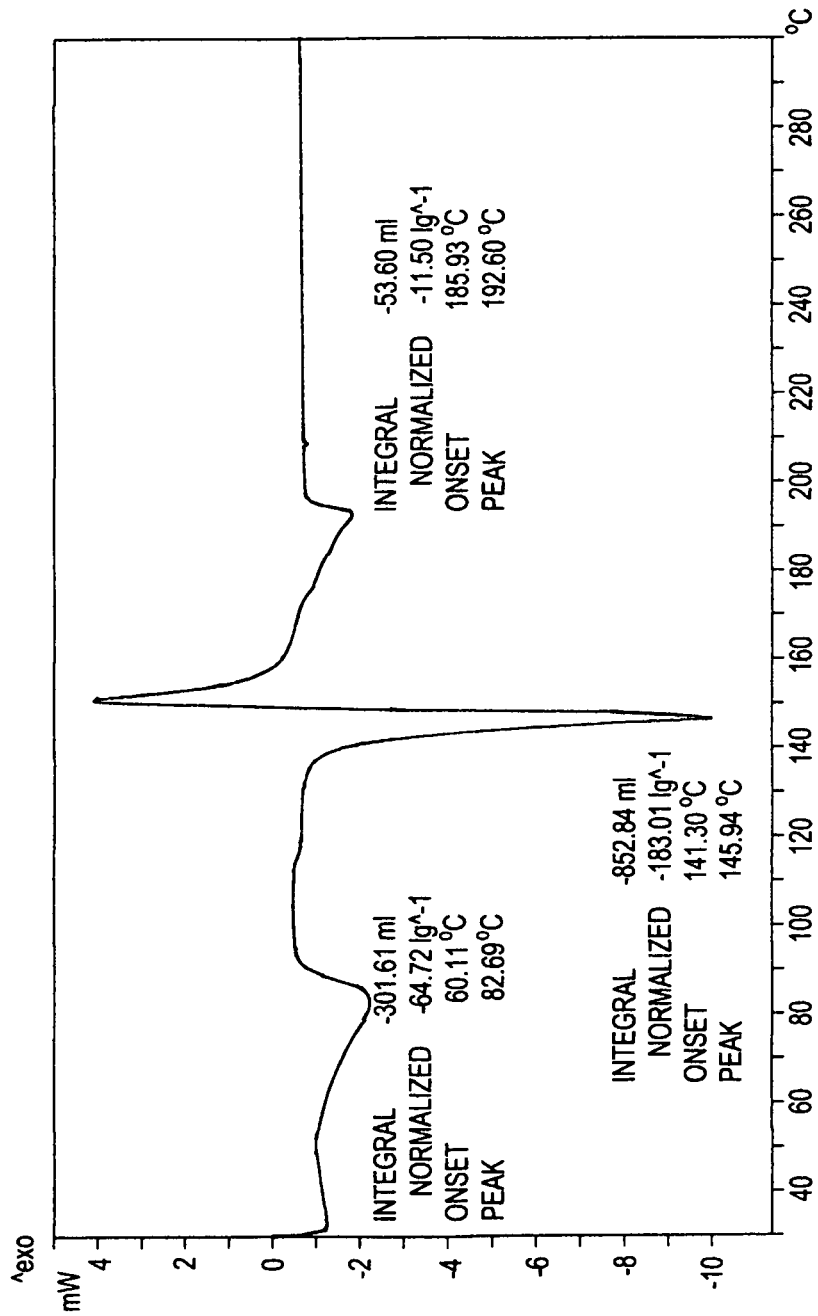
FIG. 8 is the characteristic differential scanning calorimetric (DSC) thermogram of a solid form of imatinib and caffeic acid (1:1).

In another embodiment, the present invention further provides a solid form of imatinib and caffeic acid (1:1), characterized by a differential scanning calorimetric (DSC) thermogram substantially in accordance with FIG. 8.

In another embodiment, the present invention provides a solid form of imatinib and caffeic acid (1:2).

Figure 9:
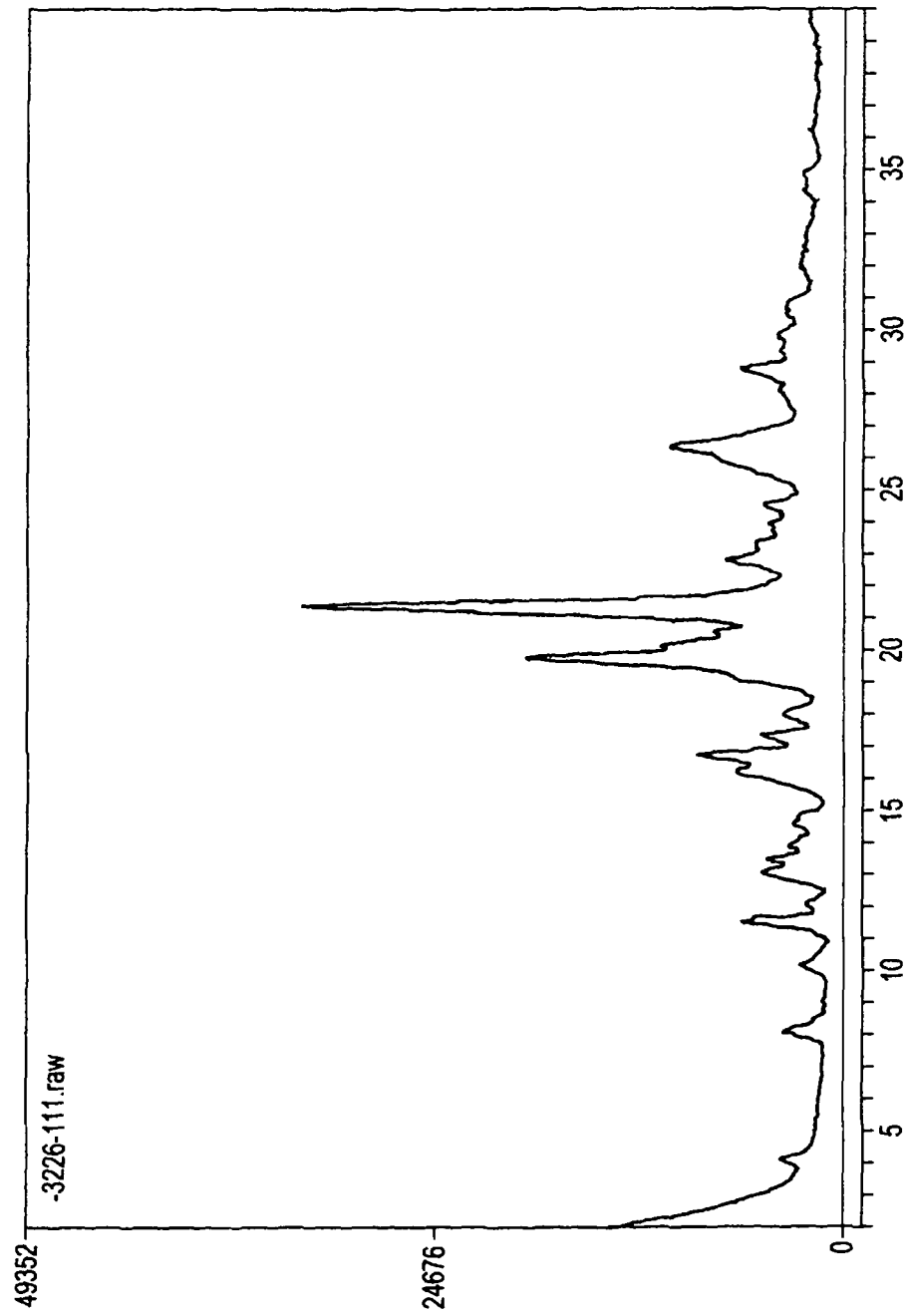
FIG. 9 is the characteristic powder X-ray diffraction (XRD) pattern of a solid form of imatinib and caffeic acid (1:2).

In another embodiment, the present invention further provides a solid form of imatinib and caffeic acid (1:2), characterized by an X-Ray diffraction (XRD) pattern substantially in accordance with FIG. 9.

Figure 10:
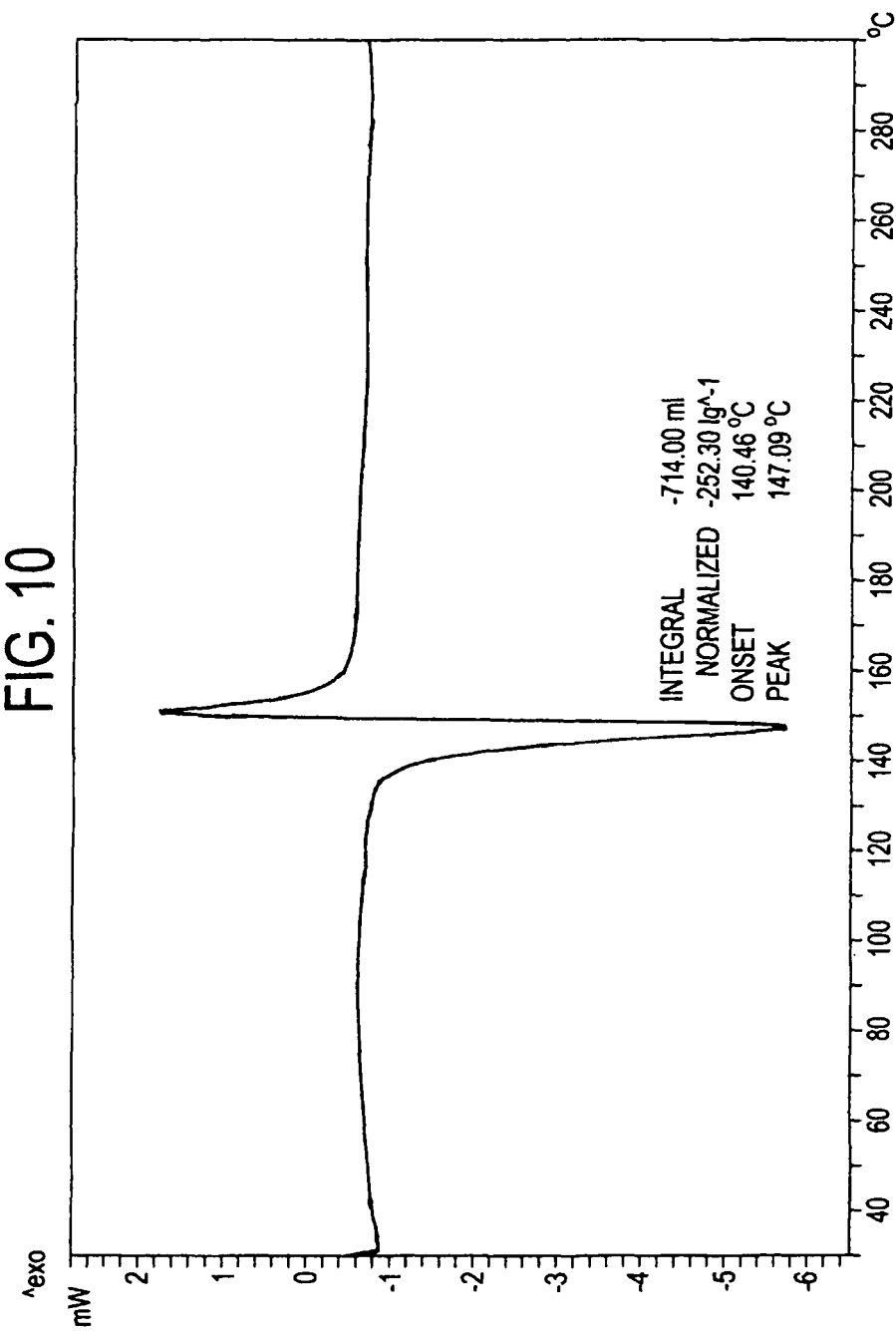
FIG. 10 is the characteristic differential scanning calorimetric (DSC) thermogram of a solid form of imatinib and caffeic acid (1:2).

In another embodiment, the present invention further provides a solid form of imatinib and caffeic acid (1:2), characterized by a differential scanning calorimetric (DSC) thermogram substantially in accordance with FIG. 10.

In another embodiment, the present invention provides a solid form of imatinib and p-coumaric acid.

Figure 11:
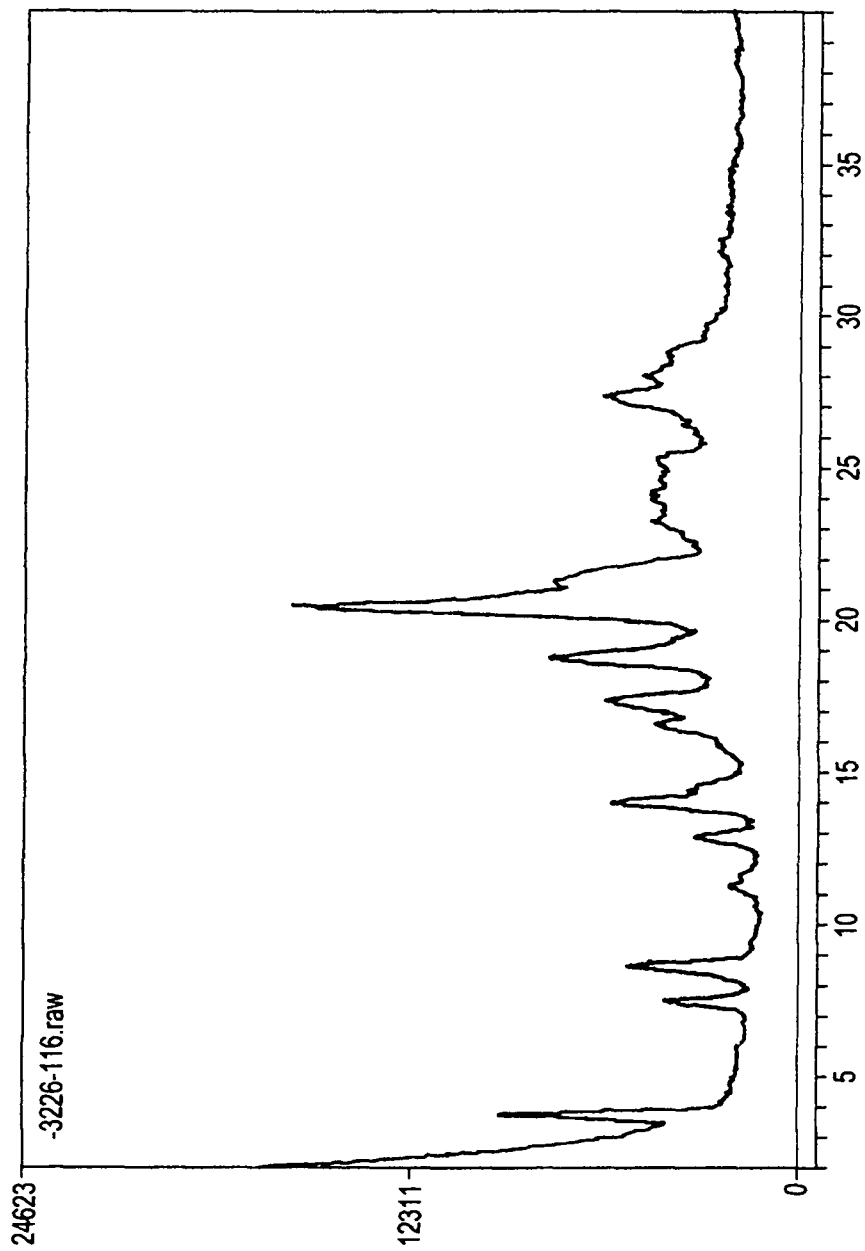
FIG. 11 is the characteristic powder X-ray diffraction (XRD) pattern of a solid form of imatinib and p-coumaric acid (1:1).

In another embodiment, the present invention further provides a solid form of imatinib and p-coumaric acid, characterized by an X-Ray diffraction (XRD) pattern substantially in accordance with FIG. 11.

Figure 12:
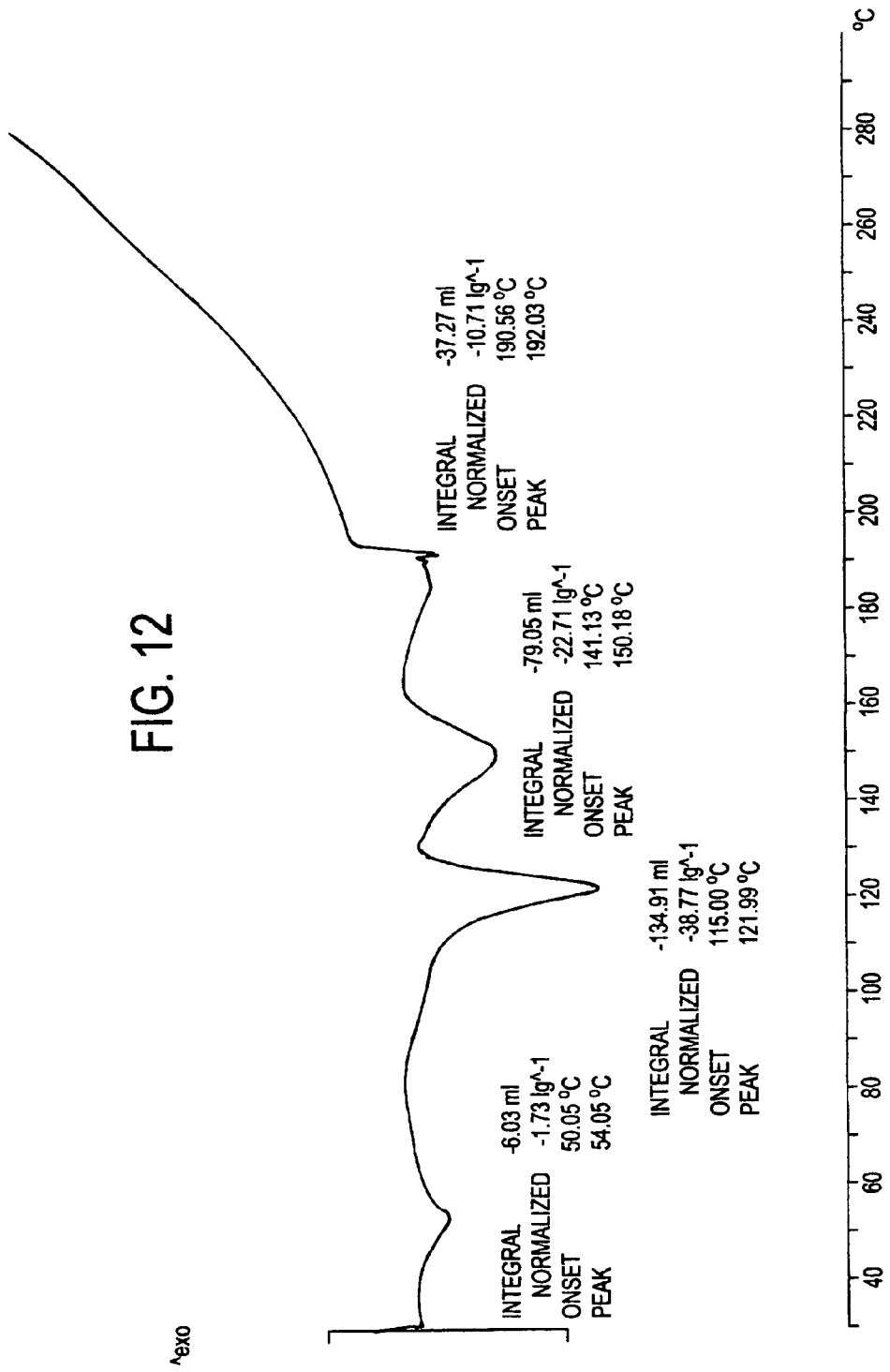
FIG. 12 is the characteristic differential scanning calorimetric (DSC) thermogram of a solid form of imatinib and p-coumaric acid (1:1).

In another embodiment, the present invention further provides a solid form of imatinib and p-coumaric acid, characterized by a differential scanning calorimetric (DSC) thermogram substantially in accordance with FIG. 12.

In another embodiment, the present invention provides a solid form of imatinib and ferulic acid.

Figure 13:
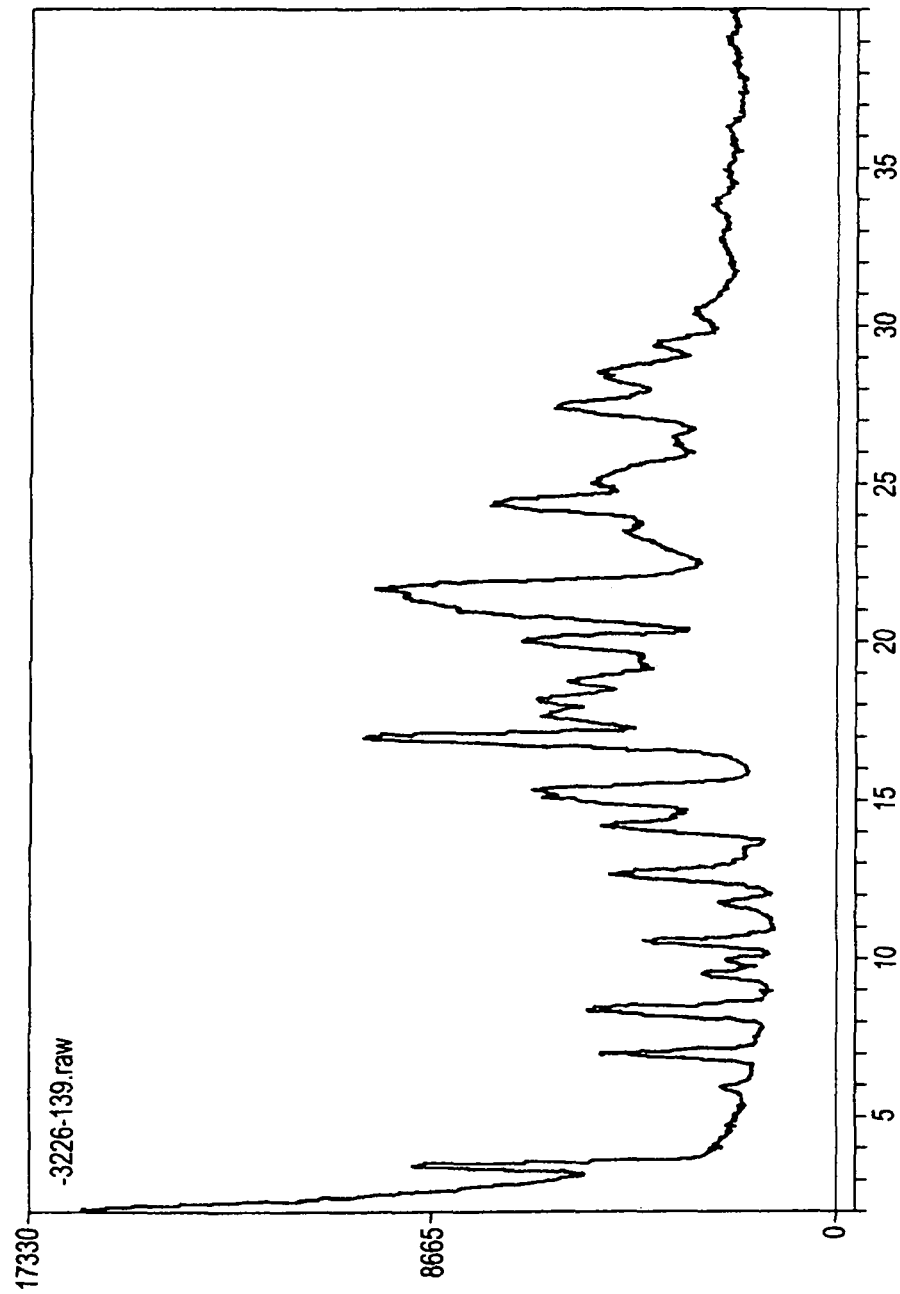
FIG. 13 is the characteristic powder X-ray diffraction (XRD) pattern of a solid form of imatinib and ferulic acid (1:1).

In another embodiment, the present invention further provides a solid form of imatinib and ferulic acid, characterized by an X-Ray diffraction (XRD) pattern substantially in accordance with FIG. 13.

Figure 14:
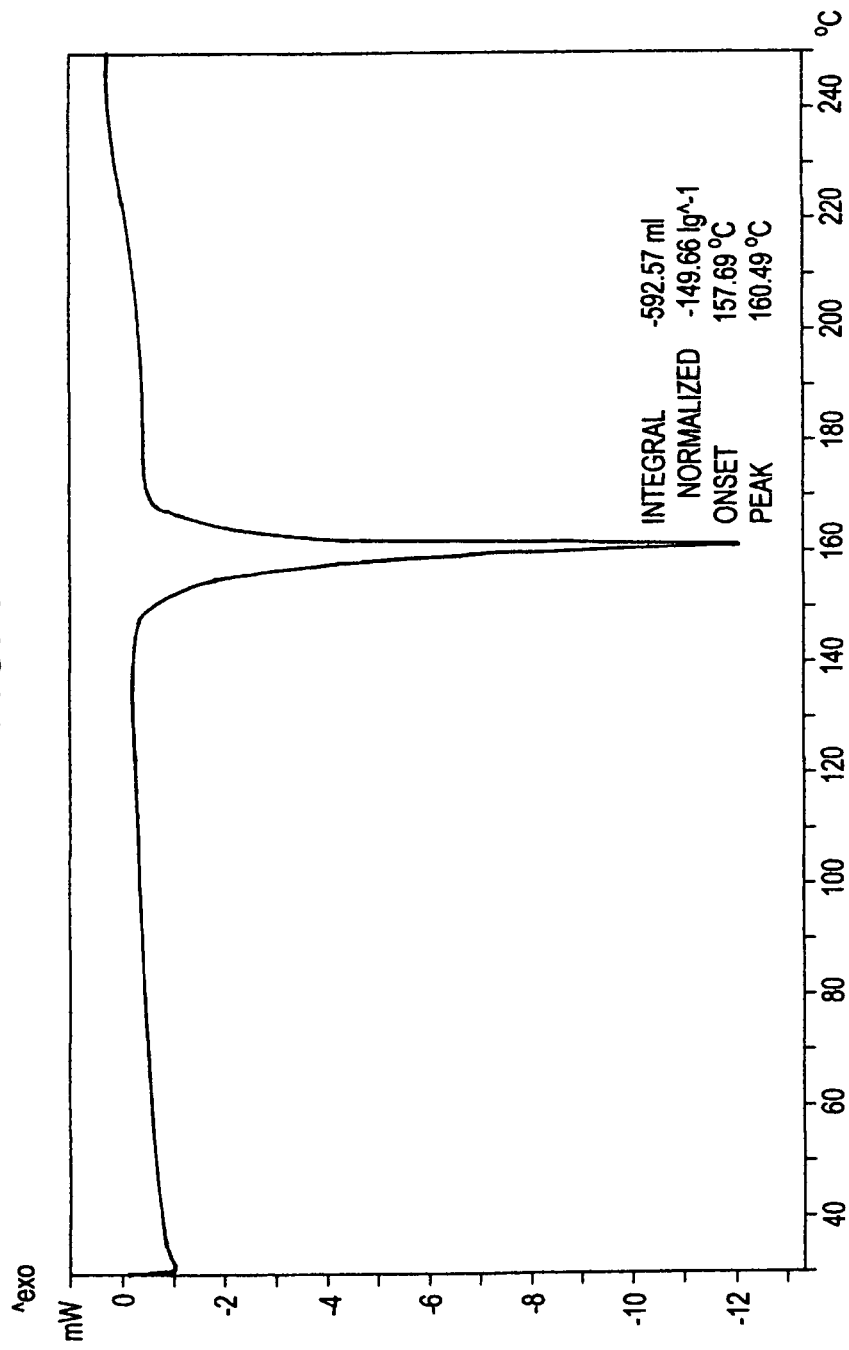
FIG. 14 is the characteristic differential scanning calorimetric (DSC) thermogram of a solid form of imatinib and ferulic acid (1:1).

In another embodiment, the present invention further provides a solid form of imatinib and ferulic acid, characterized by a differential scanning calorimetric (DSC) thermogram substantially in accordance with FIG. 14.

In another embodiment, the present invention provides characterization of solid forms of tyrosine kinase inhibitors of the present invention characterized by X-ray powder diffraction (XRD) pattern and/or melting point. The X-Ray powder diffraction can be measured by an X-ray powder Diffractometer (Bruker D8) equipped with a Cu-anode ($[\lambda]$=1.54 Angstrom), X-ray source operated at 40 kV, 30 mA and a Ni filter is used to strip K-beta radiation. Two-theta calibration is performed using an NIST SRM 640c Si standard. The sample was analyzed using the following instrument parameters: measuring range=2-40° 2θ at a scan rate 1°/minute.

In another embodiment, the present invention provides characterization of solid forms of tyrosine kinase inhibitors of the present invention characterized by a Differential Scanning calorimeter. Differential scanning calorimetry was performed on Mettler-Toledo DSC 822e module, (Mettler-Toledo, Columbus, Ohio). The temperature range for the thermogram was 30-250° C., and the sample was heated at a rate of 5° C./min.

In another embodiment, the present invention provides characterization of solid forms of tyrosine kinase inhibitors of the present invention characterized by Thermo-Nicolet 6700 FT-IR-NIR spectrometer with NXR FT-Raman module (Thermo Scientific, Waltham, Mass.) was used to record IR. IR spectra were recorded on samples dispersed in KBr pellets. Data were analyzed using the Omnic software (Thermo Scientific, Waltham, Mass.).

The solid forms described in the present invention are useful for the manufacture of solid or liquid pharmaceutical dosage forms. Each of these solid state forms possesses one or more properties that provide advantages when used as a pharmaceutical active ingredient, such as physical properties that make it easier to manufacture one or more dosage forms, improved stability, improved bioavailability and other such properties that are known to one of skill in the art.

In another embodiment, the present invention provides a pharmaceutical composition comprising a therapeutically effective amount of a solid form of a tyrosine kinase inhibitor in combination with an anti-oxidative acid, and at least one pharmaceutically acceptable carrier or excipient.

In one embodiment, the solid forms of tyrosine kinase inhibitors, particularly solid forms of gefitinib and/or imatinib, disclosed herein for use in the pharmaceutical compositions of the present invention, which may independently have a D50 and D90 particle size less than about 400 microns, preferably less than about 200 microns, more preferably less than about 150 microns, still more preferably less than about 50 microns and most preferably less than about 10 microns. Whereupon, the notation Dx means that X % of particles have a diameter less than a specified diameter D. Thus, a D50 of about 400 microns means that 50% of the micronized particles in a composition have a diameter less than about 400 microns. Any milling, grinding, micronizing or other particle size reduction method known in the art can be used to bring the solid forms of the present invention into any desired particle size range set forth above.

The term "co-crystal" as used herein means a crystalline material comprised of two or more unique solids at room temperature, each containing distinctive physical characteristics, such as structure, melting point and heats of fusion.

The following non limiting examples illustrate specific embodiments of the present invention. They are not intended to be limiting the scope of the present invention in any way.

EXAMPLE 1

Preparation of Gefitinib:Caffeic Acid (2:1)

446.9 mg of gefitinib and 10 ml of ethanol was taken in a RB flask at 25° C. to 30° C. 180 mg of caffeic acid was added at 25° C. to 30° C. The mixture was heated under reflux temperature (75° C.-80° C.) and stirred until a clear solution is obtained. The stifling was continued under reflux temperature for 2 hours. The solution was cooled to 25° C. to 30° C. and continued stifling over night (~16 hrs). The solution was filtered and washed with chilled ethanol (1 ml). The product obtained was dried at 25° C. under vacuum for 6 hours.

Yield: 523 mg (83%).

The XRPD is set forth in FIG. 1.

The DSC is set forth in FIG. 2.

IR ($Cm^{-1}$): 557, 860, 1115.2, 1231.8, 1282.5, 1326.2, 1427.8, 1441.7, 1473.7, 1500.5, 1534.7, 1578, 1628.6, 2953.8, 3442.4.

EXAMPLE 2

Preparation of Gefitinib:p-coumaric Acid (2:1)

446.9 mg of gefitinib was taken in 10 ml of ethanol at 25° C. to 30° C. in a RB flask. 164 mg of p-coumaric acid was added at 25° C. to 30° C. The mixture was heated under reflux temperature (75° C.-80° C.) and stirred until clear. The solution was stirred under reflux temperature for 1 hour. After that, the solution was cooled to 25° C. to 30° C. and continued stirring over night (~16 hrs). The solution was filtered and washed with chilled ethanol (1 ml). The product obtained was dried at 25° C. under vacuum for 6 hours.

Yield: 535 mg (87.5%).

The XRPD is set forth in FIG. 3.

The DSC is set forth in FIG. 4.

IR ($Cm^{-1}$): 836.7, 862, 1114.6, 1139.2, 1169.7, 1221, 1235.5, 1340.8, 1357.6, 1401.3, 1428.5, 1474.6, 1500, 1583.9, 1605.7, 1628.1, 2818.7, 2962, 3409.1.

EXAMPLE 3

Preparation of Gefitinib:Ferulic Acid (2:1)

446.9 mg of gefitinib was taken in 10 ml of ethanol at 25° C. to 30° C. in a RB flask. 194 mg of ferulic acid was added at 25° C. to 30° C. The mixture was heated under reflux temperature (75° C. to 80° C.) and stirred until clear. The solution was stirred under reflux temperature for 1 hour. After that, the solution was cooled to 25° C. to 30° C. and continued stiffing over night (~16 hrs). The solution was filtered and washed with chilled ethanol (1 ml). The product obtained was dried at 25° C. under vacuum for 6 hours.

Yield: 582 mg (~90%).
The XRPD is set forth in FIG. 5.
The DSC is set forth in FIG. 6.
IR (Cm$^{-1}$): 1118.3, 1219.3, 1279.4, 1428.3, 1464.2, 1475.2, 1499.2, 1562.2, 1536, 1624.6, 2956.9, 3461.3, 3742.1.

EXAMPLE 4

Preparation of Imatinib:Caffeic Acid (1:1)

5 g of imatinib was taken in 100 ml of ethanol at 25° C. to 30° C. in a RB flask. 1.825 g of caffeic acid was added. The mixture was heated under reflux temperature (75° C. to 80° C.) and stirred until a clear solution is obtained. The stirring was continued under reflux temperature for 2 hours. After that, half of the volume of the solvent was distilled out. The remaining solution was allowed to cool to 25° C. to 30° C. and continued stiffing over night (~16 hrs). The solution was filtered and washed with chilled ethanol (5 ml). The product obtained was dried at 60° C. for 6 hours.

Yield: 4.76 g (70%).
The XRPD is set forth in FIG. 7.
The DSC is set forth in FIG. 8.
IR (Cm$^{-1}$): 799.2, 987.5, 1179.5, 1203.4, 1284.8, 1302, 1330.7, 1367, 1418.2, 1450.3, 1478.5, 1532.9, 1575, 1644.4, 3262.6.

EXAMPLE 5

Preparation of Imatinib:Caffeic Acid (1:2)

1 g of imatinib was taken in 20 ml of ethanol at 25° C. to 30° C. in a RB flask. 0.73 g of caffeic acid was added. The mixture was heated under reflux temperature (75° C. to 80° C.) and stirred until clear. The stirring was continued under reflux temperature for 2 hours. After that, half of the volume of the solvent was distilled out. The remaining solution was allowed to cool to 25° C. to 30° C. and continued stirring over night (~16 hrs). The solution was filtered and washed with chilled ethanol (2 ml). The product obtained was dried at 60° C. for 6 hours.

Yield: 0.74 g (74%).
The XRPD is set forth in FIG. 9.
The DSC is set forth in FIG. 10.
IR (Cm$^{-1}$): 428, 454.9, 548, 575.5, 594.8, 635.8, 645.8, 703.3, 714.3, 751.6, 798, 850.7, 864.1, 887.2, 907.1, 976.2, 1027, 1041.6, 1106.6, 1220.7, 1302.6, 1330.2, 1449.5, 1526.8, 1574.7, 1644.7, 1677.2, 3035.3, 3287.4, 3650.5.

EXAMPLE 6

Preparation of Imatinib:p-coumaric Acid (1:1)

5 g of imatinib was taken in 12 ml of methanol and 24 ml of xylene at 25° C. to 30° C. in a 250 ml RB flask. 1.66 g of p-coumaric acid was added at 25° C. to 30° C. The mixture was heated under reflux temperature (75° C. to 80° C.) and stirred until a clear solution is obtained. The solution was stirred under reflux temperature for 2 hours. After that the solution was cooled to 25° C. to 30° C. and continued stiffing over night (~16 hrs). The solution was filtered and washed with chilled methanol/xylene (5 ml). The product obtained was dried at 60° C. under vacuum for 6 hours.

Yield: 6.2 g (94%).
The XRPD is set forth in FIG. 11.
The DSC is set forth in FIG. 12.
IR (Cm$^{-1}$): 461.3, 526.7, 649.3, 714.6, 797, 833.1, 882.2, 992.5, 1025.2, 1135.5, 1167.1, 1205, 1257.2, 1289.3, 1308.7, 1333.8, 1380, 1420.1, 1451.2, 1478.8, 1513.5, 1537.3, 1576.6, 2810.9, 2955.7, 3053, 3253.

EXAMPLE 7

Preparation of Imatinib:Ferulic Acid (1:1)

5 g of imatinib was taken in 12 ml of methanol and 24 ml of xylene at 25° C. to 30° C. in a 250 ml RB flask. 1.66 g of Ferulic acid was added at 25° C. to 30° C. The mixture was heated under reflux temperature (75° C. to 80° C.) and stirred until clear. The stiffing was continued under reflux temperature for 2 hours. After that the solution was cooled to 25° C. to 30° C. and continued stiffing over night (~16 hrs). The solution was filtered and washed with chilled methanol/xylene (5 ml). The product obtained was dried at 60° C. for 6 hours.

Yield: 6.27 g (90%).
The XRPD is set forth in FIG. 13.
The DSC is set forth in FIG. 14.
IR (Cm$^{-1}$): 705, 799.9, 820.3, 855.7, 976.4, 989.5, 1025.7, 1122.4, 1202.2, 1277.8, 1301.5, 1326.3, 1386.4, 1405.1, 1450, 1479.5, 1488.9, 1524.1, 1556.1, 1586.2, 1647.8, 2826.8, 3025.5, 3275.9, 3480.6.

While particular embodiments have been chosen to illustrate the invention, it will be understood by those skilled in the art that various changes and modifications can be made therein without departing from the scope of the invention as defined in the appended claims.

What is claimed is:

1. A pharmaceutical composition comprising an amount of a solid form of imatinib or gefitinib, and an amount of caffeic acid,
    wherein the amount of the imatinib or the gefitinib in the solid form is effective in inhibiting tyrosine kinase, and the amount of caffeic acid in the solid form is effective in improving the solubility of the imatinib or the gefitinib in water and reducing free radicals, and
    wherein the solid form of gefitinib and caffeic acid is characterized by a ratio of 2:1, an X-Ray diffraction pattern of FIG. 1, and the solid form of gefitinib used in the composition has a D50 and D90 of less than about 10 microns,
    wherein the solid form of imatinib and caffeic acid is characterized by a ratio of 1:1, an X-Ray diffraction pattern of FIG. 7, and the solid form of imatinib used in the composition has a D50 and D90 of less than about 10 microns, or
    wherein the solid form of imatinib and caffeic acid is characterized by a ratio of 1:2, an X-Ray diffraction pattern of FIG. 9, and the solid form of imatinib used in the composition has a D50 and D90 of less than about 10 microns.

2. The composition of claim 1, wherein the solid form of imatinib and caffeic acid having the ratio of 1:1 is further characterized by the differential scanning calorimetric thermogram of FIG. 8, and wherein the solid form of imatinib and caffeic acid having the ratio of 1:2 is further characterized by the differential scanning calorimetric thermogram of FIG. 10.

3. The composition of claim 1, wherein the solid form of gefitinib and caffeic acid is characterized by the differential scanning calorimetric thermogram of FIG. 2.

4. A process for preparing a solid form of a pharmaceutical composition comprising imatinib or gefitinib, and an amount of caffeic acid, comprising:
   a) providing a mixture or solution comprising the imatinib or gefitinib either in free base or a salt form, and the caffeic acid; and
   b) isolating the solid form of a composition comprising the imatinib or gefitinib and caffeic acid from the mixture or solution,
   wherein the amount of the imatinib or the gefitinib in the isolated solid form is effective in inhibiting tyrosine kinase, and the amount of caffeic acid in the isolated solid form is effective in improving the solubility of the imatinib or the gefitinib in water and reducing free radicals, and
   wherein the isolated solid form of gefitinib and caffeic acid is characterized by a ratio of 2:1, an X-Ray diffraction pattern of FIG. 1, and the solid form of gefitinib used in the composition has a D50 and D90 of less than about 10 microns,
   wherein the isolated solid form of imatinib and caffeic acid is characterized by a ratio of 1:1, an X-Ray diffraction pattern of FIG. 7, and the solid form of imatinib used in the composition has a D50 and D90 of less than about 10 microns, or
   wherein the isolated solid form of imatinib and caffeic acid is characterized by a ratio of 1:2, an X-Ray diffraction pattern of FIG. 9, and the solid form of imatinib used in the composition has a D50 and D90 of less than about 10 microns.

5. A process for preparing a pharmaceutical composition comprising a solid form of imatinib or gefitinib, and an amount of caffeic acid, comprising:
   a) providing a solid form of imatinib or gefitinib having a micronized D50 and D90 particle size of less than about 10 microns;
   b) mixing an amount of the micronized solid form of imatinib or gefitinib with an amount of caffeic acid; and
   c) forming the pharmaceutical composition from the mixture,
   wherein the amount of the imatinib or the gefitinib in the composition is effective in inhibiting tyrosine kinase, and the amount of caffeic acid in the composition is effective in improving the solubility of the imatinib or the gefitinib in water and reducing free radicals, and
   wherein the mixture of gefitinib and caffeic acid is characterized by a ratio of 2:1, and an X-Ray diffraction pattern of FIG. 1,
   wherein the mixture of imatinib and caffeic acid is characterized by a ratio of 1:1, and an X-Ray diffraction pattern of FIG. 7, or
   wherein the mixture of imatinib and caffeic acid is characterized by a ratio of 1:2, and an X-Ray diffraction pattern of FIG. 9.

* * * * *